United States Patent [19]

Flodgaard et al.

[11] Patent Number: 5,939,390

[45] Date of Patent: Aug. 17, 1999

[54] PHARMACEUTICAL COMPOSITION

[75] Inventors: Hans Flodgaard, Hellerup; Poul Baad Rasmussen, Copenhagen Ø, both of Denmark

[73] Assignee: Novo Nordisk A/S, Bagsvaerd, Denmark

[21] Appl. No.: 08/925,708

[22] Filed: Sep. 9, 1997

Related U.S. Application Data

[63] Continuation of application No. PCT/DK96/00099, Mar. 11, 1996.

[30] Foreign Application Priority Data

Mar. 9, 1995 [DK] Denmark ................................ 0240/95

[51] Int. Cl.$^6$ .................................................. A61K 38/00
[52] U.S. Cl. ...................... 514/12; 514/2; 514/8; 530/350; 530/829; 530/380
[58] Field of Search ...................... 514/12, 8, 2; 530/350, 530/829, 380

[56] References Cited

U.S. PATENT DOCUMENTS

| | | | |
|---|---|---|---|
| 5,089,274 | 2/1992 | Marra et al. | 424/534 |
| 5,484,885 | 1/1996 | Pereira et al. | 530/326 |
| 5,607,916 | 3/1997 | Pereira et al. | 514/12 |
| 5,627,262 | 5/1997 | Pereira | 530/324 |

FOREIGN PATENT DOCUMENTS

| | | |
|---|---|---|
| WO 89/08666 | 9/1989 | WIPO . |
| Wo 91/00907 | 1/1991 | WIPO . |
| WO 92/02539 | 2/1992 | WIPO . |
| WO 93/19087 | 9/1993 | WIPO . |

OTHER PUBLICATIONS

Flodgaard, H., et al. Eur. J. Biochem., vol. 197, pp. 535–547 (1991).

Hannun, Y.A., J. Biol. Chem., vol. 269, No. 5, pp. 3125–3128, (1994).

Joseph, C.K., et al., *Journal of Biol. Chem.*, vol. 269, No. 26, 17606–1710. 1994.

Pereira et al., *Proc. Natl. Acad. Sci. U.S.A.*, 90(10), 4733–7, 1993.

Hirata et al., *Endotokishin Shinpojumu Koen Kirokushu*, 7th, 17–22, 1994.

Shafer et al., (1984) Infection and Immunity 45 (1) :29–35.

Shafer et al., (1986) Infection and Immunity 53 (3) :651–655.

Dialog Information Services, file 155, Medline. Accession No. 06950917 Knoerzer et al., (1989) Gene (Netherlands) 75(1) :21–30.

Dialog Information Services, file 155, Medline. Accession No. 07793140 Rogelj et al., (1991) Methods Enzymol. (US) 198 :117–24.

*Primary Examiner*—Cecilia J. Tsang
*Assistant Examiner*—C. Delacroix-Muirheid
*Attorney, Agent, or Firm*—Steve T. Zelson, Esq.; Cheryl Agris, Esq.

[57] ABSTRACT

The present invention relates to a pharmaceutical composition for the prevention or treatment of diseases or conditions involving stress injury to cells, the composition comprising (a) a lipid-containing substance having a lipid portion which is structurally identical with or analogous to a ceramide, conjugated to (b) a protein capable of binding said lipid-containing substance in such a way that, when the conjugate is contacted with living cells, the lipid-containing substance activates a ceramide-activated protein phosphatase resulting in down-regulation of cellular metabolism, and (c) a pharmaceutically acceptable diluent or carrier.

31 Claims, 2 Drawing Sheets

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 221 amino acids
      (B) TYPE: amino acid
      (C) STRANDEDNESS: single
      (D) TOPOLOGY: linear (ii) MOLECULE TYPE: protein (vi) ORIGINAL SOURCE:
      (A) ORGANISM: human (xi) SEQUENCE DESCRIPTION: SEQ ID NO: 1:

Ile Val Gly Gly Arg Lys Ala Arg Pro Arg Gln Phe Pro Phe Leu Ala
1               5                   10                  15

Ser Ile Gln Asn Gln Gly Arg His Phe Cys Gly Ala Leu Ile His
            20                  25                  30

Ala Arg Phe Val Met Thr Ala Ala Ser Cys Phe Gln Ser Gln Asn Pro
            35                  40                  45

Gly Val Ser Thr Val Val Leu Gly Ala Tyr Asp Leu Arg Arg Arg Glu
        50                  55                  60

Arg Gln Ser Arg Gln Thr Phe Ser Ile Ser Ser Met Ser Glu Asn Gly
65                  70                  75                  80

Tyr Asp Pro Gln Gln Asn Leu Asn Asp Leu Met Leu Leu Gln Leu Asp
                85                  90                  95

Arg Glu Ala Asx Leu Thr Ser Asx Val Thr Ile Leu Pro Leu Pro Leu
                100                 105                 110

Gln Asx Ala Thr Val Glu Ala Gly Thr Arg Cys Gln Val Ala Gly Trp
            115                 120                 125

Gly Ser Gln Arg Ser Gly Gly Arg Leu Ser Arg Phe Pro Arg Phe Val
        130                 135                 140

Asx Val Thr Val Thr Pro Glu Asp Gln Cys Arg Pro Asn Asn Val Cys
145                 150                 155                 160

Thr Gly Val Leu Thr Arg Arg Gly Gly Ile Cys Asn Gly Asp Gly Gly
                165                 170                 175

Thr Pro Leu Val Cys Glu Gly Leu Ala His Gly Val Ala Ser Phe Ser
                180                 185                 190

Leu Gly Pro Cys Gly Arg Gly Pro Asp Phe Phe Thr Arg Val Ala Leu
            195                 200                 205

Phe Arg Asp Trp Ile Asp Gly Val Leu Asn Asn Pro Gly
    210                 215                 220

(2) INFORMATION FOR SEQ ID NO: 2:

(i) SEQUENCE CHARACTERISTICS:
      (A) LENGTH: 219 amino acids
      (B) TYPE: amino acid
      (C) STRANDEDNESS: single
      (D) TOPOLOGY: linear (ii) MOLECULE TYPE: protein (vi) ORIGINAL SOURCE:
      (A) ORGANISM: porcine (xi) SEQUENCE DESCRIPTION: SEQ ID NO: 2:

Ile Val Gly Gly Arg Arg Ala Gln Pro Gln Glu Phe Pro Phe Leu Ala
1               5                  10                 15

Ser Ile Gln Lys Gln Gly Arg Pro Phe Cys Ala Gly Ala Leu Val His
            20                 25                 30

Pro Arg Phe Val Leu Thr Ala Ala Ser Cys Phe Arg Gly Lys Asn Ser
        35                 40                 45

Gly Ser Ala Ser Val Val Leu Gly Ala Tyr Asp Leu Arg Gln Gln Glu
    50                 55                 60

Gln Ser Arg Gln Thr Phe Ser Ile Arg Ser Ile Ser Gln Asn Gly Tyr
65                 70                 75                 80

Asp Pro Arg Gln Asn Leu Asn Asp Val Leu Leu Gln Leu Asp Arg
                85                 90                 95

Glu Ala Arg Leu Thr Pro Ser Val Ala Leu Val Pro Leu Pro Pro Gln
            100                105                110

Asx Ala Thr Val Glu Ala Gly Thr Asn Cys Gln Val Ala Gly Trp Gly
            115                120                125

Thr Gln Arg Leu Arg Arg Leu Phe Ser Arg Phe Pro Arg Val Leu Asx
130                135                140

Val Thr Val Thr Ser Asn Pro Cys Leu Pro Arg Asp Met Cys Ile Gly
145                150                155                160

Val Phe Ser Arg Arg Gly Arg Ile Ser Gln Gly Asp Arg Gly Thr Pro
                165                170                175

Leu Val Cys Asn Gly Leu Ala Gln Gly Val Ala Ser Phe Leu Arg Arg
                180                185                190

Arg Phe Arg Arg Ser Ser Gly Phe Phe Thr Arg Val Ala Leu Phe Arg
                195                200                205

Asn Trp Ile Asp Ser Val Leu Asn Asn Pro Pro
210                215

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:3:

CCGGGGATCC GATGACCCGG CTGACAGTCC TGG                                    33

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:4:

CCCCGGGGTT CTGGCTTTGG AAGCTGCTGG CCGCGG                                 36

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:5:

```
CCGCGGCCAG CAGCTTCCAA AGCCAGAACC CCGGGG                                     36

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:6:

CCGGGGATCC AACTAGGCTG GCCCCGGTCC CGG                                        33

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:7:

GGCAGGCACT TCTCCGGAGG TGCCCTGATC                                            30

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:8:

GATCAGGGCA CCTCCGGAGA AGTGCCTGCC                                            30
```

PHARMACEUTICAL COMPOSITION

CROSS-REFERENCE TO RELATED APPLICATIONS

This application is a continuation of PCT/DK96/00099 filed Mar. 11, 1996 which claims priority under 35 U.S.C. 119 of Danish application 0240/95 filed Mar. 9, 1995, respectively, the contents of which are fully incorporated herein by reference.

FIELD OF INVENTION

The present invention relates to a pharmaceutical composition for the treatment of diseases or conditions involving stress injury to cells, and a method of treating such diseases or conditions by means of said composition.

BACKGROUND OF THE INVENTION

Septic shock resulting from a systemic response to serious infection, e.g. gram-negative bacteremia, at local sites of infection or inflammation (e.g. the abdominal cavity) with the concomitant activation of the cytokine cascade, has been increasing in incidence over the last 50 years and is currently the commonest cause of death in intensive care units in the U.S. The reasons for this increase and high incidence of septic shock are believed to be the increased use of invasive devices such as intravascular catheters, increased use of cytotoxic and immunosuppressive drugs, increased longevity of patients liable to develop sepsis and an increase in infections caused by antibiotic-resistant organisms.

Disorders associated with sepsis are bacteremia (also known as septicemia) characterized by positive blood cultures; sepsis characterized by a systemic response to the infection in the form of tachypnea, tachycardia, hyperthermia or hypothermia; sepsis syndrome in which there is clinical evidence of sepsis and signs of altered organ perfusion in the form of an abnormally increased lactate level, oliguria or acutely altered mental status; early septic shock in which there is clinical evidence of sepsis syndrome as well as hypotension lasting for less than one hour and responsive to conventional therapy; and refractory septic shock in which there is clinical evidence of sepsis syndrome and hypotension lasting for more than one hour despite conventional therapy.

The continued high mortality and morbidity attributable to gram-negative sepsis has prompted an intensive search for therapeutic agents capable of counteracting the potentially lethal effects of circulating bacterial LPS. Numerous papers report a significant therapeutical effect of high doses of intravenously administered immunoglobulin. The treatment, however, requires IgG derived from the plasma of donors screened for naturally occurring high levels of antibodies to core LPS or from very large pools of donors (>1000). Monoclonal antibodies against LPS which have also been suggested for the treatment of bacteremia (e.g. WO 88/03211) have shown little or no effect, probably because they do not inhibit the cytokine cascade induced by LPS. Furthermore, relatively few sepsis patients exhibit circulating endotoxemia and bacteremia so that antibodies neutralizing circulating LPS are not applied at the site where sepsis develops.

Mild oxidative stress is a normal feature in higher vertebrates as a result of a persistent stage of oxidative siege. Under normal conditions an efficient defense system consisting of an elaborate arsenal of antioxidants ensure that the organism is able to cope with oxygen free radicals by keeping a balance between oxygen free radicals and antioxidants. However, at sites of infection or injury, numerous aggressive oxidative species (oxygen free radicals) are secreted by phagocytes (activated neutrophil leukocytes, macrophages and monocytes) as a requisite to kill invading foreign pathogens causing infection. At these sites, the generation of oxygen free radicals is far beyond the antioxidant capacity of the surrounding cells, and these cell may be injured or die from necrosis or apoptosis (programmed cell death) mediated by oxygen free radicals.

At the site of infection or injury a cytokine cascade is initiated which, in turn, activates neutrophil leukocytes. The initiator of the cytokine cascade (in gram-negative bacteremia) is endotoxin (otherwise known as lipopolysaccharide, abbreviated to LPS) released at the infectious or inflammatory site where it induces the release of tumour necrosis factor α (TNFα), interleukin-1, interleukin-6, interleukin-8 and platelet-activating factor (PAF) from macrophages and other cells. After release of TNFα, interleukin-1 and PAF, arachidonic acid is metabolized to form leukotrienes, thromboxane $A_2$ and prostaglandins. Interleukin-1 and interleukin-6 activate T-cells to produce interferon-γ, interleukin-2, interleukin-4 and granulocyte-monocyte colony-stimulating factor. Neutrophils may be activated directly by most of these mediators. Neutrophil-induced damage may thus occur during degranulation by the release of oxygen free radicals and lysosomal enzymes, and during aggregation at infective or inflammatory sites.

Although the molecular mechanism responsible for LPS-mediated initiation of the cytokine cascade is not fully understood, recent reports of the signal transduction of the cytokines TNFα, vitD$_3$ and INF-γ shed some light on the phenomenon.

The cytokines vitD$_3$ and INF-γ have been shown to stimulate production of ceramide in HL-60 cells by stimulating a membrane-bound neutral sphingomyelinase which hydrolyses membrane sphingomyelin to ceramide and phosphorylcholine (cf. T. Okazaki et al., *J. Biol. Chem.* 265, 1990, pp. 15823–15831). Ceramide has been found to be a second messenger which, in turn, activates a ceramide-activated protein kinase belonging to the family of X Ser/Thr Pro protein kinases (cf. S. Mathias et al., *Proc. Natl. Acad. Sci. USA* 88, 1991, pp. 10009–10013). Ceramide has additionally been shown to activate a ceramide-activated Ser/Thr protein phosphatase (cf. R. T. Dobrowski and Y. A. Hannun, *J. Biol. Chem.* 267, 1992, pp. 5048–5051). These initial reactions were shown to lead to further downstream signaling in a complex and as yet poorly understood manner, involving activation of the MAP kinase cascade, stimulation of transcription factors such as c-Myc and c-Fos, activation NF-KB and stimulation of PLA$_2$ leading to the formation of arachidonic acid derivatives.

Lipoprotein-binding protein (LBP) in the circulation binds to LPS and mediates binding of LPS to the specific CD14 receptor. In a recent study of the signal transduction by LPS via the CD14 receptor on HL-60 cells, it was shown that LPS provokes its cellular responses, e.g. the initiation of the cytokine cascade by stimulation of the ceramide-activated protein kinase. Structural analysis has established that a portion of the reducing end of the lipid A moiety of LPS closely resembles a portion of ceramide (cf. C. K. Joseph et al., *J. Biol. Chem.* 269, 1994, pp. 17606–17610). It would therefore appear that LPS exerts its activity by entering into the ceramide pathway of cells.

SUMMARY OF THE INVENTION

It has surprisingly been found that LPS, when conjugated to another protein than LBP is able to mimic the second messenger function of ceramide in a different way than by activating a ceramide-activated protein kinase.

Accordingly, the present invention relates to a pharmaceutical composition for the prevention or treatment of diseases or conditions involving stress injury to cells, the composition comprising
  (a) a lipid-containing substance having a lipid portion which is structurally identical with or analogous to a ceramide, conjugated to
  (b) a protein capable of binding said lipid-containing substance in such a way that, when the conjugate is contacted with living cells, the lipid-containing substance activates a ceramide-activated protein phosphatase resulting in down-regulation of cellular metabolism, and
  (c) a pharmaceutically acceptable diluent or carrier.

In another aspect, the invention relates to a method of preventing or treating diseases or conditions involving stress injury to cells, the method comprising administering, to a patient in need of such treatment, an effective amount of
  (a) a lipid-containing substance having a lipid portion which is structurally identical with or analogous to a ceramide, conjugated to
  (b) a protein capable of binding said lipid-containing substance in such a way that, when the conjugate is contacted with living cells, the lipid-containing substance activates a ceramide-activated protein phosphatase resulting in down-regulation of cellular metabolism.

In a further aspect, the invention relates to the use of
  (a) a lipid-containing substance having a lipid portion which is structurally identical with or analogous to a ceramide, conjugated to
  (b) a protein capable of binding said lipid-containing substance in such a way that, when the conjugate is contacted with living cells, the lipid-containing substance activates a ceramide-activated protein phosphatase resulting in down-regulation of cellular metabolism,
  for the manufacture of a medicament for the prevention or treatment of diseases or conditions involving stress injury to cells.

DETAILED DISCLOSURE OF THE INVENTION

In a preferred embodiment, the composition of the invention contains, as the protein to which the lipid-containing substance is conjugated, a heparin-binding protein (HBP) which, in glycosylated form, has an apparent molecular weight of 28 kD (as determined by SDS-PAGE under reducing conditions), the protein being produced in the azurophil granules of polymorphonuclear leukocytes.

The covalent structure of heparin-binding protein isolated from peripheral neutrophil leukocytes of human and porcine origin has recently been determined (cf. H. Flodgaard et al., *Eur. J. Biochem.* 197, 1991, pp. 535–547; J. Pohl et al., *FEBS Lett.* 272, 1990, p. 200 ff.). Both the human and porcine proteins show a high similarity to neutrophil elastase, but owing to selective mutations of the active serine 195 and histidine 57 (chymotrypsin numbering (B. S. Hartley, "Homologies in Serine Proteinases", *Phil. Trans. Roy. Soc. Series* 257, 1970, p. 77 ff.)) the proteins lack protease activity. The proteins have been named human heparin-binding protein (hHBP) and porcine heparin-binding protein (pHBP), respectively, owing to their high affinity for heparin; Schafer et al. (W. M. Schafer et al., *Infect. Immun.* 53, 1986, p. 651 ff.) have named the protein cationic antimicrobial protein (CAP37) due to its antimicrobial activity. The protein has also been shown to be chemotactic for monocytes over the range $1.3 \times 10^{-9}$ M–$10^{-8}$ M (H. A. Pereira et al., *J. Clin.Invest.* 85, 1990, p.1468 ff.), consistent with the results apparent from Flodgaard et al., op. cit.

Furthermore, HBP has been shown to mediate detachment and contraction of endothelial cells and fibroblasts when added to such cells grown in monolayer culture. HBP also stimulates monocyte survival and thrombospondin secretion (E. Østergaard and H. Flodgaard, *J. Leukocyte Biol.* 51, 1992, p 316 ff).

From the azurophil granules, a protein with the first 20 N-terminal amino acid residues identical to those of hHBP and CAP37 called azurocidin has also been isolated (J. E. Gabay et al., *Proc. Natl. Acad. Sci. USA* 86, 1989, p. 5610 ff.; C. G. Wilde et al., *J. Biol. Chem.* 265, 1990, p. 2038 ff.) and its antimicrobial properties have been reported (D. Campanelli et al., *J. Clin. Invest.* 85, 1990, p. 904 ff.).

The presence of hHBP in the neutrophil leucocytes and the fact that 89% of CAP37 (which is identical to hHBP) is released when the leucocytes are phagocytosing *Staph. aureus* (H. A. Pereira et al., op cit. indicate that a function of hHBP could be its involvement in the inflammatory process since the protein is apparently released from activated neutrophils. Pereira et al., op cit., suggested a function of CAP37 to be at the site of inflammation where it could specifically attract monocytes and thus be one of the factors responsible for the influx of monocytes in the second wave of inflammation. Østergaard and Flodgaard, op. cit., suggest that, in addition to being important for the recruitment of monocytes, HBP might play a key role in the mechanism of neutrophil as well as monocyte extravasation.

Since the neutrophil leukocyte is the first cell to invade an inflammatory or infectious site where it secretes HBP, HBP-mediated cell detachment and homotypic aggregation accompanied by a downregulation of cellular metabolism may be another protective mechanism against cell injury during inflammation or infection. Once the infection has been combated, the matrix cells surviving oxidative stress due to the action of HBP are ready to re-invade the inflammatory site and contribute to the healing processes which are orchestrated by an elaborate array of growth factors and cytokines secreted from monocytes and macrophages attracted to the site by HBP.

The structure of HBP appears from WO 89/08666 and H. Flodgaard et al., op. cit. HBP has otherwise been termed CAP37 (cf. WO 91/00907) and azurocidin (cf. C. G. Wilde et al., *J. Biol. Chem.* 265, 1990, p. 2038).

HBP, in conjunction with a lipid-containing substance which may be LPS or ceramide, is currently believed to be able to downregulate cellular metabolism. LPS conjugated to HBP would appear not to bind to the LPS receptor CD14 but to the cell surface due to the strong heparan sulfate-binding motifs of HBP. New data from measurements of rapid uptake of neutrophil-derived HBP by monocytes also argue for HBP-specific ligands on monocytes that are distinct from CD14 (Heinzelmann, M. et al., Critical Care, 1996 in press). LPS is subsequently docked into the cell membrane and brought into contact with the signaling apparatus of the cell, ultimately activating a ceramide-activated protein phosphatase. Activation of the phosphatase may, in turn, lead to down-regulation of cellular metabolism. In support of this hypothesis, it has been reported that addition of exogenous ceramide made water-soluble and membrane permeable by addition of a hexanoyl group to the molecule to Swiss 3T3 cells leads to morphological changes such as contraction, detachment and homotypic aggregation with preserved cell viability. Ceramide seems to be a key regulator of antiproliferative and apoptotic pathways and as an inhibitor of protein traficking and secretion, and these events have been associated with the TNFα-induced activation of the ceramide-activated protein phosphatase via the 75 kD TNFα receptor (cf. Y. A. Hannun, *J. Biol. Chem.* 269, 1994, pp. 3125–3128). It is suggested that LPS, as a ceramide analogue, likewise stimulates the ceramide-activated protein phosphatase when conjugated to HBP.

Thus, by preparing a conjugate of HBP and LPS (or a similar lipid-containing substance), it is possible to provide a pharmaceutical composition which may be used to adjust the balance between a necessary cytokine-activated defense of the cells (mediated by stimulation of the ceramide-activated protein kinase in monocytes) and a protection of endothelial cells, smooth muscle cells and fibroblasts (mediated by stimulation of a ceramide-activated protein phosphatase) by inhibiting cell proliferation and activity at inflammatory sites. Such adjustment of the balance may be required in conditions where the cellular defence machinery does more harm than good. The direct action of HBP/LPS on endothelial cells, fibroblasts and smooth muscle cells at the inflammatory focus resulting in a "dormant" phenotype of these cells may protect them from stress injury and keep them ready to take over the repair processes once the infection has been combated.

The HBP may suitably be of mammalian, in particular human or porcine, origin. In particular, the HBP is human HBP with the amino acid sequence set forth in SEQ ID NO:1, or porcine HBP with the amino acid sequence set forth in SEQ ID NO:2, or a functional analogue or peptide fragment thereof capable of binding the lipid A portion of LPS. Examples of such functional analogues include derivatives of the native protein obtained by addition of one or more amino acid residues to either or both the C- or N-terminal end of the native protein, substitution of one or more amino acid residues at either or both ends of the native protein, deletion of one or more amino acid residues at either or both ends of the native protein or at one or more sites within the amino acid sequence, or insertion of one or more amino acid residues at one or more sites in the native amino acid sequence.

The HBP may suitably be prepared by a method described in DK patent application No. 1452/94. More specifically, a DNA sequence encoding HBP may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

The DNA sequence may also be of genomic or cDNA origin, for instance obtained by preparing a genomic or cDNA library and screening for DNA sequences coding for all or part of HBP by hybridization using synthetic oligonucleotide probes in accordance with standard techniques (cf. Sambrook et al., *Molecular Cloning: A Laboratory Manual*, 2nd Ed., Cold Spring Harbor, 1989). The DNA sequence may also be prepared by polymerase chain reaction using specific primers, for instance as described in U.S. Pat. No. 4,683,202 or R. K. Saiki et al., *Science* 239, 1988, pp. 487–491.

The DNA sequence is then inserted into a recombinant expression vector which may be any vector which may conveniently be subjected to recombinant DNA procedures. The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding HBP should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding HBP in mammalian cells are the SV 40 promoter (Subramani et al., *Mol. Cell Biol.* 1, 1981, pp. 854–864), the MT-1 (metallothionein gene) promoter (Palmiter et al., *Science* 222, 1983, pp. 809–814) or the adenovirus 2 major late promoter. A suitable promoter for use in insect cells is the polyhedrin promoter (Vasuvedan et al., *FEBS Lett.* 311, 1992, pp. 7–11). Suitable promoters for use in yeast host cells include promoters from yeast glycolytic genes (Hitzeman et al., *J. Biol. Chem.* 255, 1980, pp. 12073–12080; Alber and Kawasaki, *J. Mol. Appl. Gen.* 1, 1982, pp. 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304, 1983, pp. 652–654) promoters. Suitable promoters for use in filamentous fungus host cells are, for instance, the ADH3 promoter (McKnight et al., *The EMBO J.* 4, 1985, pp. 2093–2099) or the tpiA promoter.

The DNA sequence encoding HBP may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate.

The procedures used to ligate the DNA sequences coding for HBP, the promoter and the terminator, respectively, and to insert them into suitable vectors containing the information necessary for replication, are well known to persons skilled in the art (cf., for instance, Sambrook et al., op.cit.).

The host cell into which the expression vector is introduced may be any cell which is capable of producing HBP and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines are the COS (ATCC CRL 1650), BHK (ATCC CRL 1632, ATCC CCL 10) or CHO (ATCC CCL 61) cell lines. Methods of transfecting mammalian cells and expressing DNA sequences introduced in the cells are described in e.g. Kaufman and Sharp, *J. Mol. Biol.* 159, 1982, pp. 601–621; Southern and Berg, *J. Mol. Appl. Genet.* 1, 1982, pp. 327–341; Loyter et al., *Proc. Natl. Acad. Sci. USA* 79, 1982, pp. 422–426; Wigler et al., *Cell* 14, 1978, p. 725; Corsaro and Pearson, *Somatic Cell Genetics* 7, 1981, p. 603, Graham and van der Eb, *Virology* 52, 1973, p. 456; and Neumann et al., *EMBO J.* 1, 1982, pp. 841–845.

Alternatively, fungal cells (including yeast cells) may be used as host cells. Examples of suitable yeast cells include cells of Saccharomyces spp. or Schizosaccharomyces spp., in particular strains of *Saccharomyces cerevisiae*. Examples of other fungal cells are cells of filamentous fungi, e.g. Aspergillus spp. or Neurospora spp., in particular strains of *Aspergillus oryzae* or *Aspergillus niger*. The use of Aspergillus spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g. in catalogues of the American Type Culture Collection).

The HBP produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, affinity chromatography, or the like.

In a preferred embodiment of the present invention, the lipid-containing substance is LPS. LPS suitable for inclusion in the composition of the invention may be obtained from the cell wall of gram-negative bacteria. Alternatively, the lipid-containing substance may be the Lipid A portion of LPS. Lipid A may suitable be prepared by synthesizing Lipid X which is a precursor of Lipid A. The synthesis of Lipid X is described in I. Macher, *Carbohydrate Res.* 162, 1987, pp. 79–84, and K. Ikeda et al., *Chem. Pharm. Bull.* 35, 1987, pp. 1383–1387. Lipid A is synthesized by reacting UDP-Lipid X in the presence of a crude preparation of Lipid A synthetase from *E. coli*, as described in P. L. Stuetz et al. in "Cellular and Molecular Aspects of endotoxin reactions", Eds. A. Nowotny, J. J. Spitzer and E. J. Ziegler, 1990, pp. 129–145. Furthermore, the lipid-containing substance may be a ceramide. Ceramide belongs to the group of sphingolipids, a chemically diverse class of biomolecules including compounds, such as ceramide phosphate and galactosylceramide. Preferred ceramides have the structure $$R^3R^4CH-CH-CH_2OR^2$$
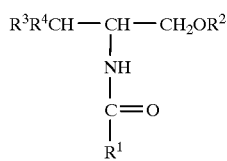

wherein $R^1$ is a linear or branched, saturated or unsaturated $C_{14-30}$-alkyl which may be substituted in the α-position by a hydroxyl group or esterified in the ω-position by a saturated or unsaturated $C_{16-30}$ fatty acid;

$R^{2'}$ is a hydrogen atom or a phosphate group;

$R^3$ is $C_{15-26}$ alkyl which may be saturated or unsaturated in the α-position or substituted by a hydroxy group in the α-position and optionally substituted by one or more $C_{1-14}$ alkyl groups, or $R^3$ is an aryl group, preferably a phenyl group, which may be substituted by hydroxyl, halogen, including F, Cl, and Br, or methyl; and $R^4$ is hydrogen or a hydroxyl group. More preferred ceramides have the structure

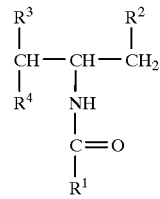

wherein $R^1$ is $C_{14}$ alkyl, $R^2$ is hydrogen or a hydroxyl or phosphate group, $R^3$ is $C_{15}$-alkyl or phenyl, and $R^4$ is hydrogen or a hydroxyl group. A preferred ceramide is N-hexanoylsphingosine ($C_6$-ceramide).

Various ceramides may be synthesized by, e.g., substitution on carbon 2 ($R^1$) with various chain length fatty acids as described in P. Van Veldhoven et al., *Anal. Biochem.* 183, 1989, pp. 177–189, who use acylation of D-erythrosphingosine with the anhydride form of the fatty acid wanted. The substitution on carbon 3 ($R^3$, $R^4$) has been described in A. Bielawska et al., *J. Biol. Chem.* 267, 1992, pp. 18493–18497, and A. Bielawska et al., *J. Biol. Chem.* 268, 1993, pp 26226–26232.

In the pharmaceutical composition the conjugate may be formulated by any of the established methods of formulating pharmaceutical compositions, e.g. as described in *Remington's Pharmaceutical Sciences*, 1985. The composition may typically be in a form suited for local or systemic injection or infusion and may, as such, be formulated with sterile water or an isotonic saline or glucose solution. The compositions may be sterilized by conventional sterilization techniques which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc. The concentration of HBP may vary widely, i.e. from less than about 0.5%, such as from 1%, to as much as 15–20% by weight. A unit dosage of the composition may typically contain from about 10 mg to about 1 g of HBP.

The pharmaceutical composition of the invention is contemplated to be advantageous to use for therapeutic applications such as treatment of inflammation, viral infection, ischemic reperfusion syndrome, bacterial endotoxaemia, sepsis, septic shock, disseminated intravascular coagulation or for stimulating a patient's immune system by activation of monocytes. For this purpose, a daily dosage of the conjugate of 1–100 mg/kg body weight is contemplated to be suitable, dependent on the severity of the condition to be treated and the patient's condition.

The invention is further illustrated in the following example which is not in any way intended to limit the scope of the invention as claimed.

EXAMPLE 1
Double-mutated HBP ($Cys^{26,42}$)

The LPS binding site in HBP is flanked by the two cysteines, $Cys^{26}$ and $Cys^{42}$. In order to make a HBP derivative unable to bind LPS the two cysteines were altered to serines by PCR mutagenesis: The transfer construct pVL1392-HBP was used as template in the first round of mutagenesis where $Cys^{42}$ was altered. In two PCR reactions with Pfu polymerase and the two pairs of primers PBRa 247 (CCGGGGATCCGATGACCCGGCTGACAGTCCTGG) (SEQ ID NO:3)/PBRa 259 (CCCCGGGGTTCTGGCTT-TGGAAGCTGCTGGCCGCGG) (SEQ ID NO:4) and PBRa 260 (CCGCGGCCAGCAGCTTCCAAAGCCAG-AACCCCGGGG) (SEQ ID NO:5)/PBRa 246 (CCGGGGATCCAACTAGGCTGGCCCCGGTCCCGG) (SEQ ID NO:6) two overlapping fragments each containing the mutation were generated. One tenth of each fragment was added to a new PCR reaction with the primers PBRa 246 and PBRa 247. The resulting full-length DNA fragment was digested with BamHI and ligated into pVL1393 in the correct orientation. The mutation was confirmed by sequencing and the transfer construct was designated pVL1393-HBP-$Cys^{42}$. In order to also change $Cys^{26}$ in pVL1393-HBP-$Cys^{42}$ two overlapping primers, PBRa 261 (GGCAGGCACTTCTCCGGAGGTGCCCTGATC) (SEQ ID NO:7) and PBRa 262 (GATCAGGGCACCTCCGGAGAAGTGCCTGCC) (SEQ ID NO:8), were used together with PBRa 246 and PBRa 247, respectively, in a new round of PCR mutagenesis as described above. Again the generated full-length DNA fragment was cloned into the BamHI site of pVL1393 and the mutation was confirmed by sequencing (pVL1393-HBP-$Cys^{26,42}$). Co-transfecting SF9 insect cells with linearized AcRP23.lacZ baculovirus DNA (Pharmingen, San Diego) and pVL1393-HBP-$Cys^{26,42}$ recombinant baculovirus encoding the double mutated HBP derivative was isolated.

In order to produce this double mutated form of HBP $3 \times 10^8$ SF9 cells growing in supplemented Grace's medium (Gibco) with 10% FCS were centrifuged down and resuspended in a sample from the virus stock giving a MOI (multiplicity of infection) of 1. The cells with virus were transferred to a 0.5 l Bellco spinner flask (#1965–00500), and fresh supplemented Grace's medium with 2% FCS was added to a final volume of 300 ml. Finally 1.5 g Heparin Sepharose (CL-6B, Pharmacia), which had been autoclaved in 25 ml sterile 0.9% NaCl, was added to the culture. The culture was incubated at 27° C. for 3 days.

To isolate the Heparin Sepharose beads from the insect cell culture the 400 ml volume was centrifuged in 50 ml tubes in a Sorvall Instruments TECHNOSPIN R centrifuge at 300 rpm for 3 min. The supernatants with cells were sucked away and the pelleted heparin Sepharose beads were separated from the remainder of contaminating cells by resuspension in 30 ml 0.9% NaCl added to each tube followed by centrifugation at 300 rpm. The entire procedure was repeated twice. The beads were finally washed in 20 ml sterile 0.5 M NaCl added to each tube. The beads were then collected in one 50 ml tube in a small volume of 0.5 M sterile NaCl (20–30 ml) and transferred to a sterile glass filter funnel. The beads were allowed to drain and the HBP mutant was finally eluted from the beads with 30 ml sterile 3 M NaCl. The HBP mutant was purified from the 3 M eluate according to the method described in WO 89/08666.

The HBP mutant material was tested for LPS binding capacity using the assay described below, and no LPS binding was observed.

Assay for LPS Binding Capacity

The binding experiments were performed in 155 μl of sterile 0.9% NaCl containing Bovine serum albumine (Sigma St. Louis Mo.) 1 mg/ml, 4.5 picomol [$^3$H] lipopolysaccharide from Escherichia coli K12 LCD25 Lot#5102A, specific activity $1.45 \times 10^6$ dpm/microgram, List Biological Laboratories, Inc., CA, USA and the following amounts of the HBP mutant: 0 pmol (control) 35 pmol, 18 pmol and 3.6 pmol. The mixture was incubated for 20 min at 37° C. using a waterbath. Ten μg of a rabbit polyclonal anti HBP antibody was added to each sample in a volume of 10 μl and incubation for 60 min. at room temperature was performed. Eight mg Protein A Sepharose (Pharmacia Sweden) was finally added to each sample in a volume of 50 μl. After incubation for 10 min. at room temperature the Protein A Sepharose/anti HBP antibody complex was spun down at 2000×g for 5 min. and the radioactivity in the supernatant was determined by counting an aliqout of 100 μl supernatant from each sample in of Beta Scintillation Counter (Packcard Instrument). From the counts remaining in the supernatant the binding of lipopolysaccharide was calculated on the assumption of a mole to mole reaction.

The HBP mutant material was tested for its ability to mediate cell detachment and homotypic aggregation on fibroblasts and endothelial cells as described by Østergaard and Flodgaard, op. cit.

No effect could be observed, supporting the idea that a conjugate between HBP and LPS is necessary for mediating these effects.

EXAMPLE 2
Recombinant Wildtype and Chimeric HBP

Recombinant human wildtype HBP was produced using a baculovirus expression system in insect cells (SF.9/BRL). HBP was purified as previously described (1).

Aiming at perturbing the putative LPS binding site in HBP without altering the overall folding of the molecule, a chimeric form of HBP was constructed. The loop encompassing aa 26–42 (HBP-numbering) in the family of chymotrypsin like proteases is highly variable (2). It has been suggested that the effector site in HBP is situated within this loop, which also contains the LPS binding site (2). Pereira et al (2) have shown that besides the importance of the conserved cysteine bridge in this loop, the RH motif in the sequence QGRHF just prior to the first C in the loop is important for LPS binding as well.

In order to create a molecule devoid of LPS binding, without disturbing the overall structure of the molecule, a loop containing less polar amino acids at the same place was introduced from another serine protease. The porcine kallikrein sequence YSSPQ fulfils this requirement. Furthermore, the packing of this loop to the rest of the molecule seems to fit well, deduced from molecular modeling using the program Portage Quanta. Thus, the chimeric form of HBP had the five amino acids QGRHF preceding $Cys^{26}$ substituted with YSSPQ.

Endothelial Cell Culture

Human umbilical vein endothelial cells (HUVEC) were isolated and cultured as previously described (3) with some modifications (4). Briefly, umbilical cords were collected in $Ca^{2+}$ and $Mg^{2+}$-free PBS and stored at 4° C. until cell isolation. The umbilical cords were used within 24 h. The veins were rinsed with $Ca^{2+}$ and $Mg^{2+}$-free PBS prior to incubation with collagenase diluted in PBS at a final concentration of 70 U/ml at 37° C. Released cells were centrifuged, suspended in medium 199 supplemented with fetal bovine serum (8%), calf serum (8%), heparin (16

U/ml), endothelial cell growth supplement (25 μg/ml) and antibiotics (penicillin 83 U/ml, streptomycin 83 μg/ml and fungizone 83 μg/ml) and seeded into 83-cm² flasks pre-coated with 2% gelatin in PBS. After 3–7 days of culture, the cells were detached using trypsin-EDTA (0.05%:0.5 mM) and seeded into 48-well plated. In some experiments, the cells were passed once before seeded into 48-well plates. The cells were used when expressing cobblestone morphology.

Protein Phosphorylation in Intact Cells

Confluent HUVECs grown in 48-well plates were washed twice with phosphate-free buffer consisting of glucose (5.56 mM), NaCl (117.2 mM), $CaCl_2$ (1.8 mM), $MgCl_2$ (0.81 mM), KCl (5.36 mM), $NaHCO_3$ (17.9 mM) and HEPES (10 mM) at pH 7.4 and then incubated with 25 μCi $^{32}PO_4$ in phosphate-free buffer supplemented with 10% human heat-inactivated serum for 30 min at 37° C. The reagents were added to the HUVECs and allowed to incubate for another 30 min. Okadaic acid was diluted in 10% dimethyl sulfoxide and used at a final concentration of 1 μM okadaic acid in 0.16 % dimethyl sulfoxide. Ceramide was dissolved in ethanol:dodecane (98:2 v/v) (13) and the final concentration of ethonol and dodecane was 0.98% and 0.02%, respectively. The final concentration of human heat-inactivated serum was 10% in all incubations. At the end of the experiment, the HUVECs were washed twice with ice-cold phosphate-free buffer and once with ice-cold PBS. Electrophoresis sample buffer (190 μl) (14) containing 5% SDS was added to the wells and HUVEC were lysed overnight at room temperature on a shaker.

Separation and Analysis of $^{32}PO_4$-labelled Proteins $^{32}PO_4$-labelled proteins were reduced by β-mercaptoethanol (5%) and separated by 4-16% SDS polyacrylamide gel electrophoresis (SDS-PAGE) (5). The electrophoresis gels were stained with Coomassie blue, dried and exposed to X-ray film or Fuji-Imaging plates. Quantitative analysis of dominating radioactive proteins with a $M_r$ range of 18–90 was done on gels exposed to Fuji Imaging plates on a BioImaging Analyzer Bas2000 (Fuji Photo Film Co., Ltd., Tokyo, Japan). Radioactivity was expressed as percentage of control. The average change in radioactivity in selected protein bands (between three to seven different proteins) was calculated.

LPS-binding Capacity of Chimeric HBP

The affinity of wildtype HBP binding for LPS has earlier been shown (6). Binding of chimeric and wildtype HBP to LPS immobilized on microtiter plates was performed using a modification of a procedure described previously by Tobias et al (7). Briefly, microtiter plates were coated overnight at 37° C. with 4 μg/well of LPS in 50 mM borate (pH 9.0) and 20 mM EDTA. Binding of HBP to uncoated wells were included to determine non-specific binding. The plates were washed extensively by distilled and deionized water, allowed to dry at 37° C. and then blocked for 30 min at 37° C. with 5 mg/ml very low endotoxin bovine serum albumin prepared in pyrogen-free PBS. The plates were then washed four times in assay buffer which consisted of pyrogen-free 50 mM Tris (pH 7.4), 500 mM NaCl, 1 mg/ml very low endotoxin bovine serum albumin and 0.05% Tween-20. Wildtype recombinant [$^{125}$I] HBP and chimeric [$^{125}$I] HBP, with specific activity 5322 and 5445 cpm/ng HBP, respectively, were diluted in assay buffer and added to the wells at indicated concentrations in a total volume of 100 μl per well. After 1 h of incubation at 37° C., the plates were washed three times in assay buffer and 100 μl 20% SDS was added to each, well followed by shaking for 10 min at room temperature. The radioactivity of the SDS solutions was determined in a γ-counter (Packard Instrument). In contrast to wildtype HBP, only minor amounts of chimeric HBP bound to the immobilized LPS (FIG. 1).

Statistical Analysis

Significance of differences between experimental groups was determined. Data were examined by the Kruskal-Wallis one-way analysis of variance followed by multiple comparisons on ranks using the Mann-Whitney U-test or by the Mann-Whitney U-test alone. Results are given as arithmetic means ±SD.P-values <0.05 were considered statistically significant.

Chimeric HBP Lacking LPS Binding

We have earlier shown that wildtype HBP binds LPS (6). In order to investigate whether the binding of LPS to HBP is important for the effect of HBP on protein phosphorylation a chimeric HBP was constructed which failed to bind LPS (FIG. 1). In contrast to wildtype HBP, the chimeric HBP did not decrease protein phosphorylation in endothelial cells (FIG. 2), indicating that an intact LPS binding domain in HBP indeed was essential for the effect on protein phosphorylation. The decreased protein phosphorylation induced by wildtype HBP (50 μg/ml) was significantly different from both chimeric HBP (50 μg/ml) and the control (n=4, p=0.0209). These experiments were performed in the presence of okadaic acid (1 μM), and similar results were observed also in the absence of okadaic acid (data not shown).

REFERENCES

Figure 1:
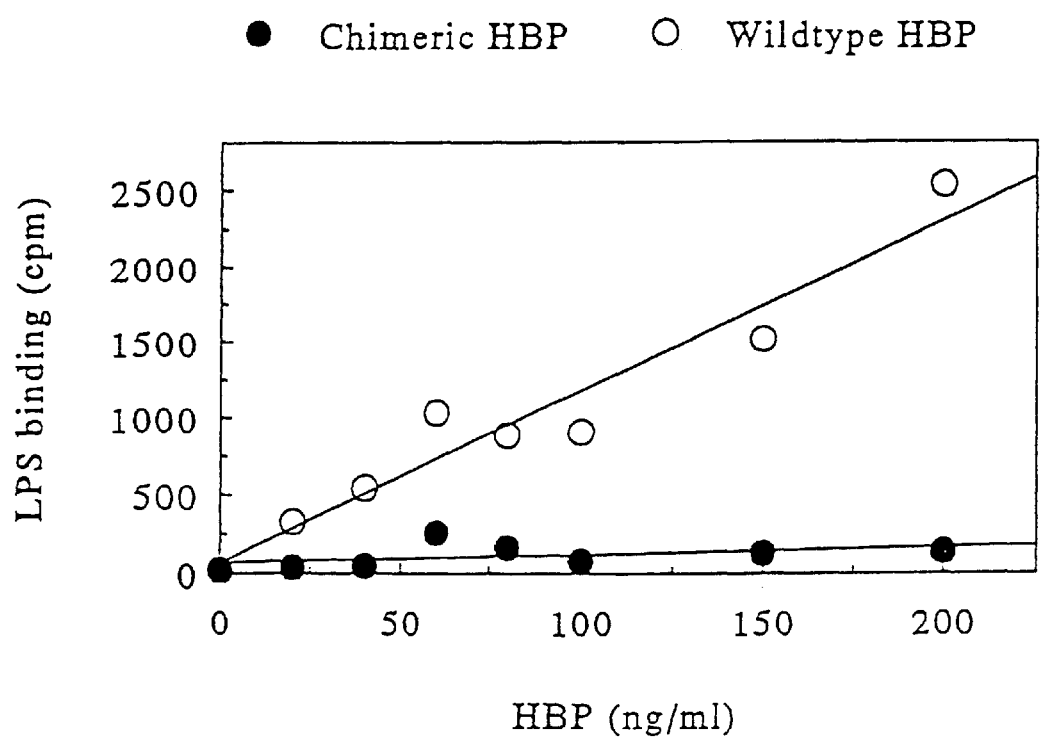
FIG. 1 Chimeric HBP did not bind to lipopolysaccharide. Binding of $^{125}$I-labelled wildtype and chimeric HBP to LPS immobilized on a microtiterplate for 1 h was studied in duplicates. Wildtype HBP dose dependently bound to LPS, whereas only little binding of chimeric HBP to LPS was seen. The figure shows the mean binding in duplicate wells from one experiment.
Figure 2:
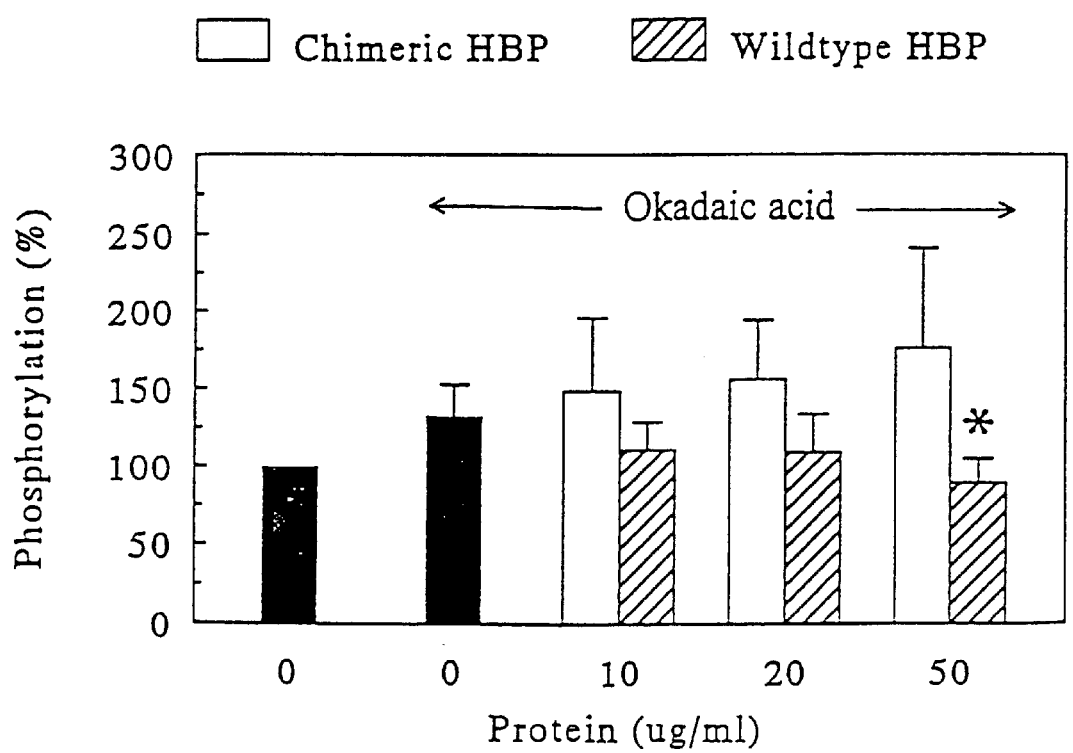
FIG. 2 Chimeric HBP, lacking lipopolysaccharide binding capacity, was unable to decrease protein phosphorylation. Endothelial cells were labelled with $^{32}PO_4$ for 30 minutes followed by incubation with okadaic acid alone (1 μM) or okadaic acid in combination with indicated concentrations of wildtype HBP or chimeric HBP for another 30 min. Radioactive proteins were separated by 4–16% SDS-PAGE and analyzed by a Phospho-Imager. The mean ± SD of four individual experiments are shown. The results show that chimeric HBP, in contrast to wildtype HBP, was unable to decrease protein phosphorylation. The Mann-Whitney U-test was done after the Kruskal-Wallis test, and wildtype HBP (50 μg/ml) was significantly different from both chimeric HBP (50 μg/ml) and control (n=4, P=0.0209).

1. Flodgaard, H., Östergaard, E., Bayne, S., Svendsen, A., Thomsen, J., Engels, M. and Wollmer, A. (1991) *Eur. J. Biochem.* 197, 535–547
2. Pereira, H. A., Erdem, I., Pohl, J. and Spitznagel, J. K. (1993) *Proc. Natl. Acad. Sci. USA* 90, 4733–4737
3. Jaffe, E. A., Nachman, R. L., Becker, C. G. and Minick, C. R. (1973) *J. Clin. Invest.* 52, 2745–2756
4. Thornton, S. C., Mueller, S. N. and Levine, E. M. (1983) *Science* 222, 623–625
5. Laemmli, U. K. (1970) *Nature* 227, 680–685
6. Flodgaard, H and Goriche, C. (1994) *J. Cell Biochem. Suppl* 18 A, Abstr E505
7. Tobias, P. S., Soldau, K. and Ulevitch, R. J. (1989) *J. Biol. Chem.* 264, 10867–10871

We claim:

1. A pharmaceutical composition for the prevention or treatment of diseases or conditions involving stress injury to cells, the composition comprising
    (a) a lipid-containing substance having a lipid portion which is structurally identical with or analogous to a ceramide, conjugated to
    (b) heparin-binding protein (HBP) or an analogue thereof capable of binding said lipid-containing substance, which conjugate when contacted with living cells, the lipid-containing substance activates a ceramide-activated protein phosphatase resulting in down-regulation of cellular metabolism, and
    (c) a pharmaceutically acceptable diluent or carrier.

2. A composition according to claim 1, wherein the protein to which the lipid-containing substance is conjugated is a heparin-binding protein which, in glycosylated form, has an apparent molecular weight of 28 kD as determined by SDS-PAGE under reducing conditions, the protein being produced in the azurophil granules of polymorphonuclear leukocytes.

3. A composition according to claim 2, wherein the heparin-binding protein is human HBP.

4. A composition according to claim 3, wherein the HBP has the amino acid sequence set forth in SEQ ID NO:1, or an analogue thereof capable of binding the lipid-containing substance.

5. A composition according to claim 2, wherein the heparin-binding protein is porcine HBP.

6. A composition according to claim 5, wherein the HBP has the amino acid sequence set forth in SEQ ID NO:2 or an analogue thereof capable of binding the lipid-containing substance.

7. A composition according to claim 1, wherein the lipid-containing substance is lipopolysaccharide (LPS).

8. A composition according to claim 1, wherein the lipid-containing substance is the lipid A portion of LPS.

9. A composition according to claim 1, wherein the lipid-containing substance is a ceramide.

10. A composition according to claim 9, wherein the ceramide has the structure

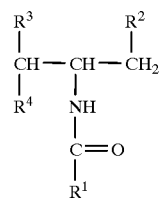

wherein $R^1$ is an amide-linked fatty acid with a chain length of 14 carbon atoms, $R^2$ is hydrogen or a hydroxyl or phosphate group, $R^3$ is $C_{15}$-alkyl or phenyl, and $R^4$ is hydrogen or a hydroxyl group.

11. A composition according to claim 9, wherein the ceramide has the structure

19

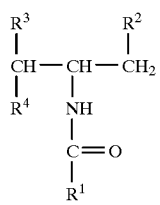

wherein
- $R^1$ is a linear or branched, saturated or unsaturated $C_{14-30}$-alkyl which may be substituted in the α-position by a hydroxyl group or esterified in the ω-position by a saturated or unsaturated $C_{16-30}$ fatty acid;
- $R^2$ is a hydrogen atom or a phosphate group;
- $R^3$ is $C_{15-26}$ alkyl which may be saturated or unsaturated in the α-position and optionally substituted by one or more $C_{1-14}$ alkyl groups, or $R^3$ is an aryl group; and
- $R^4$ is hydrogen or a hydroxyl group.

12. The composition according to claim 9 wherein the ceramide has the structure

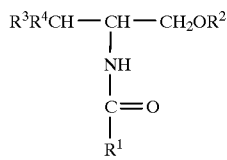

wherein
- $R^1$ is a linear or branched, saturated or unsaturated $C_{14-30}$-alkyl which may be substituted in the α-position by a hydroxyl group or esterified in the ω-position by a saturated or unsaturated $C_{16-30}$ fatty acid;
- $R^2$ is a hydrogen atom or a phosphate group;
- $R^3$ is $C_{15-26}$ alkyl which may be saturated or unsaturated in the α-position and optionally substituted by one or more $C_{1-14}$ alkyl groups, or $R^3$ is a substituted or unsubstituted phenyl group; and
- $R^4$ is hydrogen or a hydroxyl group.

13. The composition according to claim 12, wherein $R^3$ is a phenyl group substituted with a hydroxyl, halogen or methyl.

14. The composition according to claim 12, wherein $R^3$ is a phenyl group substituted with a halogen selected from the group consisting of F, Cl and Br.

15. A method of preventing or treating diseases or conditions involving stress injury to cells, the method comprising administering, to a patient in need of such treatment, an effective amount of
(a) a lipid-containing substance having a lipid portion which is structurally identical with or analogous to a ceramide, conjugated to
(b) a heparin-binding protein which, in glycosylated form, has an apparent molecular weight of 28 kD, the protein being produced in the azurophil granules of polymorphonuclear leukocytes and is capable of binding said lipid-containing substance in such a way that, when the conjugate is contacted with living cells, the lipid-containing substance activates a ceramide-activated protein phosphatase resulting in down-regulation of cellular metabolism.

16. A method according to claim 15, wherein the heparin-binding protein is human HBP.

20

17. A method according to claim 15, wherein the heparin-binding protein has the amino acid sequence set forth in SEQ ID NO:1, or an analogue thereof capable of binding the lipid-containing substance.

18. A method according to claim 15, wherein the heparin-binding protein is porcine HBP.

19. A method according to claim 15, wherein the HBP has the amino acid sequence set forth in SEQ ID NO:2 or an analogue thereof capable of binding the lipid-containing substance.

20. A method according to claim 15, wherein the lipid-containing substance is lipopolysaccharide.

21. A method according to claim 15, wherein the lipid-containing substance is the lipid A portion of LPS.

22. A method according to claim 15, wherein the lipid-containing substance is a ceramide.

23. A method according to claim 22, wherein the ceramide has the structure

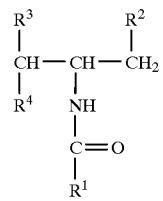

wherein $R^1$ is an amide-linked fatty acid with a chain length of 14 carbon atoms, $R^2$ is hydrogen or a hydroxyl or phosphate group, $R^3$ is $C_{15-26}$ alkyl or phenyl, and $R^4$ is hydrogen or a hydroxyl group.

24. A method according to 15 in which said diseases or conditions are selected from the group consisting of inflammation, viral infection, ischaemic reperfusion syndrome, sepsis, septic shock, and disseminated intravascular coagulation.

25. A method according to claim 15, wherein the effective amount of the protein/lipid-containing substance conjugate is in the range of from about 1 mg to about 100 mg/kg body weight.

26. The method according to claim 15, wherein the ceramide has the structure

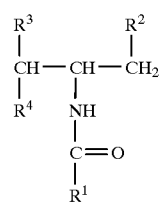

wherein
- $R^1$ is a linear or branched, saturated or unsaturated $C_{14-30}$-akyl which may be substituted in the α-position by a hydroxyl group or esterified in the ω-position by a saturated or unsaturated $C_{16-30}$ fatty acid;
- $R^2$ is a hydrogen atom or a phosphate group;
- $R^3$ is $C_{15-26}$ alkyl which may be saturated or unsaturated in the α-position and optionally substituted by one or more $C_{1-14}$ alkyl groups, or $R^3$ is aryl group; and
- $R^4$ is hydrogen or a hydroxyl group.

27. The method according to claim 15, wherein the ceramide has the structure

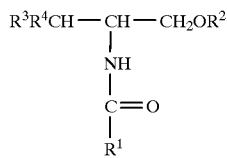

wherein
- $R^1$ is a linear or branched, saturated or unsaturated $C_{14-30}$-alkyl which may be substituted in the α-position by a hydroxyl group or esterified in the ω-position by a saturated or unsaturated $C_{16-30}$ fatty acid;
- $R^2$ is a hydrogen atom or a phosphate group;
- $R^3$ is $C_{15-26}$ alkyl which may be saturated or unsaturated in the αposition and optionally substituted by one or more $C_{1-14}$ alkyl groups, or $R^3$ is a substituted or unsubstituted phenyl group; and
- $R^4$ is hydrogen or a hydroxyl group.

28. The method according to claim 27, wherein $R^3$ is a phenyl group substituted with a hydroxyl, halogen or methyl.

29. The method according to claim 27, wherein $R^3$ is a phenyl group substituted with a halogen selected from the group consisting of F, Cl and Br.

30. A method for activating a ceramide-activated protein phosphatase such that there is down-regulation of cellular metabolism in a patient in need thereof, comprising administering to said patient an effective amount of (a) a lipid-containing substance having a lipid portion which is structurally identical with or analogous to a ceramide, conjugated to (b) a heparin-binding protein which, in glycosylated form, has an apparent molecular weight of 28 kD, the protein being produced in the azurophil granules of polymorphonuclear leukocytes and is capable of binding said lipid-containing substance in such a way that, when the conjugate is contacted with living cells, the lipid-containing substance activates a ceramide-activated protein phosphatase resulting in down-regulation of cellular metabolism.

31. A method for stimulating a patient's immune system comprising administering to a patient in need thereof an effectve amount of (a) a lipid-containing substance having a lipid portion which is structurally identical with or analogous to a ceramide, conjugated to (b) a heparin-binding protein which, in glycosylated form, has an apparent molecular weight of 28 kD, the protein being produced in the azurophil granules of polymorphonuclear leukocytes and is capable of binding said lipid-containing substance in such a way that, when the conjugate is contacted with living cells, the lipid-containing substance activates a ceramide-activated protein phosphatase resulting in down-regulation of cellular metabolism.

* * * * *